United States Patent [19]
Cherukuri et al.

[11] Patent Number: 4,981,698
[45] Date of Patent: Jan. 1, 1991

[54] MULTIPLE ENCAPSULATED SWEETENER DELIVERY SYSTEM AND METHOD OF PREPARATION

[75] Inventors: Subraman R. Cherukuri, Towaco; Tommy K. Chau, Bridgewater; Krishna P. Raman, Randolph; Angel M. Orama, Stanhope, all of N.J.

[73] Assignee: Warner-Lambert Co., Morris Plains, N.J.

[21] Appl. No.: 452,660

[22] Filed: Dec. 18, 1989

Related U.S. Application Data

[63] Continuation-in-part of Ser. No. 329,742, Mar. 28, 1989, Pat. No. 4,933,190, which is a continuation-in-part of Ser. No. 945,743, Dec. 23, 1986, Pat. No. 4,816,265.

[51] Int. Cl.$^5$ .............................................. A23G 3/30
[52] U.S. Cl. .......................................... 426/5; 426/3; 426/548; 426/804; 426/96; 426/99; 426/307; 426/660; 426/549; 424/48; 424/52
[58] Field of Search ..................... 426/3, 5, 548, 804, 426/96, 99, 307, 549, 660; 424/48, 52

[56] References Cited

U.S. PATENT DOCUMENTS

| | | | |
|---|---|---|---|
| 3,389,000 | 6/1968 | Fujita et al. | 426/99 |
| 3,527,647 | 9/1970 | Hager | 426/453 |
| 3,867,556 | 2/1975 | Darragh et al. | 426/98 |
| 3,949,094 | 4/1976 | Johnson et al. | 426/99 |
| 3,976,794 | 8/1976 | Johnson et al. | 426/307 |
| 4,105,801 | 8/1978 | Dogliotti | 426/99 |
| 4,122,195 | 10/1978 | Bahoshy et al. | 426/3 |
| 4,139,639 | 2/1979 | Bahoshy et al. | 426/548 |
| 4,293,572 | 10/1981 | Silva et al. | 426/307 |
| 4,374,858 | 2/1983 | Glass et al. | 426/5 |
| 4,382,924 | 5/1983 | Berling et al. | 424/180 |
| 4,384,004 | 5/1983 | Cea et al. | 426/5 |
| 4,597,970 | 7/1986 | Sharma | 426/5 |
| 4,933,190 | 6/1990 | Cheruhuri et al. | 426/5 |

FOREIGN PATENT DOCUMENTS

0053844 6/1982 European Pat. Off. ............ 426/548

Primary Examiner—Jeanette Hunter
Attorney, Agent, or Firm—Daniel A. Scola, Jr.

[57] ABSTRACT

A delivery system for one or more sweeteners offers enhanced up front sweetness intensity in combination with prolonged sweetness duration, and improved protection and stability of the active. The delivery system comprises a first high intensity sweetener encapsulated in a first core coating, and a second outer hydrophilic coating containing up to the solubility limit of the second coating of a second sweetener. The resulting delivery system may be incorporated into a variety of comestible products including chewing gums and other confections, baked goods, oral pharmaceuticals and oral hygiene preparations.

32 Claims, 2 Drawing Sheets

MULTIPLE ENCAPSULATED SWEETENER DELIVERY SYSTEM AND METHOD OF PREPARATION

The present Application is a Continuation-in-Part of Co-pending application Ser. No. 329,742, filed Mar. 28, 1989 now U.S. Pat. No. 4,933,190, which is in turn a Continuation-in-Part of Co-pending application Ser. No. 945,743, filed Dec. 23, 1986 now U.S. Pat. No. 4,816,265, both in the names of Subraman Rao Cherukuri and Gul Mansukhani. Applicants claim the benefit of both applications under 35 U.S.C. 120.

BACKGROUND OF THE INVENTION

The present invention relates generally to a sweetener delivery system and, more particularly, to an artificial sweetener composite that offers a combination of improved up front and controlled release with improved stability and shelf life.

Numerous patents have disclosed coatings for sweeteners in an attempt to delay or prolong sweetness, as well as to stabilize those sweeteners, such as aspartame, which are sensitive to moisture, temperature and pH. U.S. Pat. No. 4,384,004 to Cea et al. discloses solid particles of aspartame encapsulated by a coating material selected from the group consisting of cellulose, cellulose derivatives, arabinogalactin, gum arabic, polyolefins, waxes, vinyl polymers, gelatin, zein and mixtures thereof, wherein the amount of said coating material to said methyl ester is from 1:1 to 1:10. More particularly, the coating materials include cellulose, methyl cellulose, ethyl cellulose, cellulose nitrate, cellulose acetate phthalate, carboxymethyl cellulose, hydroxyethyl cellulose, hydroxypropyl cellulose, arabinogalactin; polyethylene, polymethacrylates, polyamides, ethylene-vinyl acetate copolymers, polyvinylpyrrolidone; gum arabic, paraffin wax, carnauba wax, spermaceti, beeswax; stearic acid, steryl alcohol, glyceryl stearate; gelatin, zein and mixtures thereof.

The method of coating employed in this reference includes suspending the aspartame particles in a stream of air that passes through a zone of atomized liquid droplets of the coating material, so that the coating material is deposited on the surface of the aspartame. More than one coating may be used, and in such instance, the inner coating is preferably water-soluble and the outer coating is preferably water-insoluble.

U.S. Pat. Nos. 4,122,195 and 4,139,939, both to Bahoshy et al., fix aspartame by preparing it with a material such as gum arabic or the reaction product of a compound containing a polyvalent metallic ion, with an ungelatinized starch acid-ester of a substituted dicarboxylic acid, by a spray drying technique, where the aspartame and a film former are prepared in an emulsion.

U.S. Pat. No. 4,374,858 to Glass et al. discloses an aspartame sweetened chewing gum having improved sweetness stability wherein the chewing gum piece has aspartame coated on its surface, as opposed to incorporating it in the chewing gum mix.

European Patent Application No. 81110320.0, published June 16, 1982 (Publication No. 0053844) to Ajinomoto Co., Inc., discloses a stabilized dipeptide-based sweetening composition comprising (1) from 20 to 60% by weight of solid fat, (b) from 10 to 30% by weight emulsifier, (c) from 10 to 30% by weight polysaccharide and (d) not more than 30% by weight of dipeptide sweetener. The compositions are prepared by heating the mixture of the ingredients, cooling, and pulverizing to obtain powder or granules of the composition to obtain an ASTM mesh size of smaller than 12. Spray drying the mixture is also disclosed.

U.S. Pat. No. 4,105,801 to Degliotti discloses a confection comprising a core portion and a shell adherently enveloping the core portion, whereby the shell is formed by an intimate mixture of microcrystals of xylitol with a solid fatty substance in a proportion of 0.5 to 15 parts by weight of fatty substance to each 100 parts by weight of xylitol. The fatty substance is preferably a mono-, di- or triglyceride having a melting range of between 20° and 60° C.

U.S. Pat. No. 3,389,000 to Toyonaka et al. discloses protective coatings for granular nucleoside-5-phosphates, the coatings being edible fats melting between 40°-100° C. and derived from plants and animals. Examples of edible fats include hydrogenated oils such as soybean oil, cottonseed oil, almond oil, castor oil, linseed oil, mustard oil, olive oil, grapefruit seed oil, palm oil, palm kernel oil, rapeseed oil, rice bran oil and the like and mixtures thereof. This reference discloses a process of preparing the granular product from a liquid mixture of fats and nucleoside-5-phosphates which are sprayed from a pressure nozzle and the resultant granules cooked and recovered.

U.S. Pat. No. 4,382,924 to Berling discloses liquid oral dosage forms for vitamins or pharmaceutical materials comprising an edible oil, a high potency lipid soluble sweetener such as saccharin and a lipid soluble flavorant. The edible oil may be a polyol fatty acid ester having at least four fatty acid ester groups and each fatty acid having from about 8 to about 22 carbon atoms. The oil, sweetener and flavor oil are mixed and heated and then cooled to provide a palatable liquid dosage form.

For a general discussion of spraying fatty materials onto sweeteners and the like, see U.S. Pat. Nos. 3,949,094 and 3,976,794 both to Johnson and U.S. Pat. No. 3,867,556 to Darragh et al. U.S. Pat. No. 4,293,572 to Silva et al. discloses the application of a dispersion of an emulsified fat with a solution of dextrin, saccharin or a polysaccharide to a food product as a barrier against moisture. U.S. Pat. No. 3,527,647 discloses a process of agglomerating particles by randomly scattering and spraying moistened particles to cause them to collide and form agglomerates.

The problem relating to stabilization of sweeteners such as aspartame, which has not been previously addressed, relates to the wettability of the aspartame crystal as well as to its morphological configuration. As a result, it is very difficult to coat aspartame using ordinary mixing or spray coating techniques. To be effective as protective barriers, coatings must be able to wet and adhere to the crystalline surface, including the needle-like tips and other shape variations of the aspartame. Additionally, the coating must be capable of being applied in a film with a uniform thickness sufficient to provide a barrier against degradative factors such as moisture, pH changes, temperature changes and reactive chemicals. The coatings, in addition to being protective barriers, must be flexible enough to conform to the surface irregularities and geometrical configuration without cracking due to mechanical stresses which it is subjected to during incorporation of the sweetener into specific product applications.

One approach has been to mix known coating materials such as fats, with certain other core materials such as aspartame, however the noted coating materials do not provide adequate protection to keep the core material in a stabilized state. Fats do not provide adequate coating materials, nor do such coating materials as starch and certain other materials such as waxes. Many of these materials require solvents and moisture for application, which have adverse effects on the stability of hydrophilic instable materials such as aspartame.

The process of European Patent Application No. 81110320.9 (Publication No. 0053844) filed Dec. 10, 1981, discussed above, is an example of admixing of coating materials with aspartame. This publication discloses the melting and admixture of from 20 to 60% of solid fat, 10 to 30% of polysaccharide and not more than 30% dipeptide sweetener. The mixture is then cooled and pulverized or spray dried. The pulverizing into fine powder, however, results in rupturing of the coating, leaving the aspartame exposed. Spray drying is normally associated with the driving off of moisture or solvents.

U.S. Pat. No. 4,597,970 discloses a delivery system wherein a sweetener is coated with a mixture of fatty acid or wax, lecithin and monoglyceride. The delivery system of this reference discloses a method of protecting the sweetener as well as providing controlled release.

The prior art techniques for coating difficult-to-coat materials such as aspartame has focused on two methods. The first method involves the formation of a molten mixture of the coating material with the sweetener. The mixture is then solidified by cooling and pulverizing. The resultant particles represent a random attempt at completely coating or enrobing the sweetener. In the case of aspartame, this coating does not provide adequate protection against moisture or aldehyde-containing flavor oils and instability of the aspartame results.

The second conventional prior art technique for coating materials involves fluidized bed spray coating. This technique involves suspending a mass of the material to be coated into a stream of atomized droplets of coating material. In the case where this process is employed with uncoated materials such as aspartame, this method is very difficult. Aspartame is a low density material, has a large surface to weight ratio and poor wetting characteristics.

In earlier filed co-pending application Ser. No. 945,743, it was proposed to prepare a sweetener delivery system comprising a sweetener such as aspartame dispersed in a melted and blended mixture of a low molecular weight polyvinylacetate and an emulsifier. The resulting dispersion is then cooled to ambient temperature and hardened, and thereafter ground to the desired particle size. Optionally, the particles thus prepared were coated with a hydrophobic mixture comprising a fat or wax blended with an emulsifier to provide, in effect, a discrete second coating to the sweetener composite. While the resulting composite exhibits improved stability, particularly when the subsequent coating of the fat/wax mixture is employed, the application of the latter coating tended to further delay sweetness release. This additional delay of release is undesirable in certain products, such as chewing gums and other confections, where a more immediate sweetness release is desired.

A further drawback in the use of the fat/wax second coating is that substantial amounts of this coating must be applied to the core particle to provide the required protection to the sweetener, particularly in the instance where the sweetener is aspartame. Thus, it has been found necessary to apply fat/wax coatings of about 300% by weight of the initial low molecular weight polyvinylacetate coating to confer the desired stability to the sweetener. The application of a coating of such thickness, even by the improved spray congealing methods utilized, is a relatively complex and involved procedure which naturally adds to the cost of the resulting product and consequently to products into which such sweetener composite may be incorporated.

A last concern respecting the composites prepared in accordance with co-pending application Ser. No. 945,743 by the incorporation of a subsequent coating of fat/wax, relates to the high temperature sensitivity of such a resulting composite. In particular, the fat/wax coating is more temperature sensitive and therefore the resulting sweetener composite cannot be employed in certain products such as baked goods or hard candies where higher processing temperatures are involved, without some concern that the outer coating of the composite will melt and thereby increase the risk that the sweetener will be attacked and broken down.

In later filed co-pending application Ser. No. 329,742, the properties of the earlier composite were modified and improved by the preparation of a sweetener-containing composite, differing in the application of a hydrophilic outer coating. The resulting composite provides improved temperature stability and greater initial sweetness release in combination with the desired delay in release of the active within the core. It would be desirable however, to improve the up front sweetness release of this composite, and it is to this and related objectives that the present invention is directed.

SUMMARY OF THE INVENTION

It has been discovered that a sweetener delivery system can be made using a multiple coating system comprising a first inner or core coating and a second outer coating prepared from a solution of a hydrophilic polymer having a quantity of a sweetener dissolved therein. The core coating may comprise a hydrophobic material such as a fat or wax, or a hydrophilic material such as a hydrocolloid. Suitable hydrocolloids include gums, pectins, alginates, mucilages, film forming carbohydrates, and mixtures. A particular core material comprises a coating containing a sweetener formed from the combination of an emulsifier with low molecular weight polyvinyl acetate.

This multiple coating system provides improved resistance to attack from the flavor component when the present delivery system is incorporated into a chewing gum, and improved stability at high temperatures. When applied to sweeteners such as aspartame, these coatings effectuate sustained release of the sweetener and thereby extend the period of sweetener perception and enjoyment of the chewing gum or confection, while at the same time enhancing the initial intensity and experience of sweetness release by the inclusion of the separate quantity of the second sweetener in the outer hydrophilic coating.

In the instance where a different sweetener is included in the outer coating, the respective sweeteners will be sequentially released and a favorable sweetness sensation resulting from the corresponding differences in the attributes of the sweeteners will be apparent. The sweetener delivery system of the present invention can be used in both sugar gums and in sugarless gum formulations.

In its broadest aspect, the sweetener delivery system of the present invention comprises:

A. At least one first solid natural or artificial high intensity sweetener selected from the group consisting of amino acid-based sweeteners, chloro derivatives of sucrose, dihydroflavinol, hydroxyguaiacol esters, L-aminodicarboxylic acid gem-diamines, L-aminodicarboxylic acid aminoalkenoic acid ester amides, dipeptide sweeteners, glycyrrhizin, saccharin and its salts, acesulfame salts, cyclamates, steviosides, talin, dihydrochalcone compounds and mixtures thereof;

B. An inner coating selected from hydrophobic and hydrophilic coating materials, the inner coating and the first sweetener mixed and prepared to form a core with the first sweetener present in a amount of from about 1% to about 50% by weight and preferably from about 1% about 30% by weight of said core; and C. A outer coating of a hydrophilic polymer containing a second sweetener, the outer coating prepared from a solution of the hydrophilic polymer and the second sweetener, with the second sweetener being present in the polymer solution in an amount ranging from about 10% to about 25% by weight as based on said solution, and preferably from about 3% to about 15% as based on said solution, the outer coating present in an amount of from about 5% to about 50% by weight and preferably from about 15% to about 50% by weight of the inner coating.

Suitable coating materials for the preparation of the inner coating may include hydrophobic resins, fats and waxes, while suitable hydrophilic materials include cellulosics, alginates, gums, pectins, mucilages, film forming carbohydrates, and mixtures. Other hydrophilic coating materials include vinyl polymers such as polyvinyl pyrrolidine and polyvinyl acetate, the latter set forth herein in accordance with a particular embodiment of the invention.

In the instance where polyvinyl acetate is the core coating, the delivery system comprises:

A. At least one first solid natural or artificial high intensity sweetener selected from the group consisting of amino acid-based sweeteners, chloro derivatives of sucrose, dihydroflavinol, hydroxyguaiacol esters, L-aminodicarboxylic acid gem-diamines, L-aminodicarboxylic acid aminoalkenoic acid ester amides, dipeptide sweeteners, glycyrrhizin, saccharin and its salts, acesulfame salts, cyclamates, steviosides, talin, dihydrochalcone compounds and mixtures thereof;

B. An emulsifier selected from the group consisting of lecithin, stearates, ester derivatives of stearates, palmitates, ester derivatives of palmitates, oleates, ester derivatives of oleates, glycerides, ester derivatives of glycerides, sucrose polyesters, polyglycerolesters, and animal waxes, vegetable waxes, synthetic waxes, petroleum wax and mixtures thereof;

C. A first inner coating of polyvinyl acetate present in amounts of about 20% to about 93% by weight of the total composition and having a molecular weight of about 2,000 to about 14,000 and preferably about 2,000 to about 12,000; and D. A second outer coating of a hydrophilic polymer containing a second sweetener, the outer coating prepared from a solution of the hydrophilic polymer and the second sweetener, with the second sweetener being present in the polymer solution in an amount ranging from about 10% to about 25% by weight as based on said solution, and preferably from about 3% to about 15% as based on said solution, the outer coating present in an amount of from about 5% to about 50% by weight and preferably from about 15% to about 50% by weight of the inner coating.

The combination of polyvinyl acetate and aforementioned emulsifiers and the outer hydrophilic coating produces a coating system that forms excellent films on the sweeteners. The core coatings of this embodiment are substantially water-insoluble and thus protect the sweetener or other encapsulated material from hydrolytic degradation. Yet, these core coatings possess sufficient hydrophilic character to swell in the presence of water, thereby slowly releasing the core material. Other advantages of the core coating can be enumerated. For example, the coatings are non-cariogenic and the method of making the delivery system does not employ the use of solvents.

The hydrophilic outer coating may comprise a hydrocolloid. The hydrocolloid may be generally selected from the group consisting of gums, pectins, alginates, mucilages, film forming carbohydrates, and mixtures thereof.

The hydrophilic outer coating confers the combined advantages of more rapid disintegration and corresponding acceleration of sweetener release while at the same time providing improved heat stability and resistance to sweetener breakdown from flavor attack. Also, the presence of the sweetener in the outer coating enhances up front sweetness release, and in the instance where the core sweetener differs from the coating sweetener, the transition between the respective sweeteners enhances overall sweetness perception.

The present delivery system may be incorporated into a variety of confections including hard and soft candies, chewing gums and particularly, low calorie, low moisture formulations, as well as in pharmaceutical preparations, personal hygiene products, and as a part of tablet coatings where it is desirable to enhance the intensity of up front sweetener delivery and prolong the duration of sweetener delivery, and to improve the stability of the sweetener by minimizing the interaction of the sweetener with both the flavor and moisture.

The delivery system of the present invention may be used alone or in combination with conventional sweeteners in various edible products. For example, the present invention includes a chewing gum comprising a gum base, a flavor, the present sweetener delivery system and optionally, additional sweeteners, fillers, and other additives. Both sugar containing and sugarless gums are contemplated, including gums with high gum base-low carbohydrate content.

Accordingly, it is a principal object of the present invention to provide a sweetener delivery system that offers a combination of improved up front sweetness with prolongation of sweetness sensation.

It is a further object of the present invention to provide a sweetener delivery system as aforesaid which provides improved stability to the intense sweetener in the core.

It is a still further object of the present invention to provide chewing gum compositions or other comestible products, pharmaceutical products or oral hygiene products, each having contained therein the sweetener delivery system of the present invention.

Other objects and advantages will become apparent to those skilled in the art from a consideration of the ensuing description which proceeds with reference to the following illustrative drawings.

DETAILED DESCRIPTION

In accordance with the present invention, a sweetener delivery system is disclosed which exhibits a combination of improved properties including increased up front sweetener presentation and prolonged sweetener delivery, and improved temperature stability. The sweetener delivery system of the present invention broadly comprises:

A. At least one first solid natural or artificial high intensity sweetener selected from the group consisting of amino acid-based sweeteners, chloro derivatives of sucrose, dihydroflavinol, hydroxyguaiacol esters, L-aminodicarboxylic acid gem-diamines, L-aminodicarboxylic acid aminoalkenoic acid ester amides, dipeptide sweeteners, glycyrrhizin, saccharin and its salts, acesulfame salts, cyclamates, steviosides, talin, dihydrochalcone compounds and mixtures thereof;

B. A first inner coating selected from hydrophobic and hydrophilic coating materials, the inner coating and the first sweetener mixed and prepared to form a core with the first sweetener present in an amount of from about 1% to about 50% by weight, and preferably from about 1% to about 30% by weight of said core; and C. A second outer coating of a hydrophilic polymer containing a second sweetener, the outer coating prepared from a solution of the hydrophilic polymer and the second sweetener, with the second sweetener being present in the polymer solution in an amount ranging from about 10% to about 25% by weight as based on said solution, and preferably from about 3% to about 15% as based on said solution, the outer coating present in an amount of from about 5% to about 50% by weight and preferably from about 15% to about 50% by weight of the first coating.

In the instance where the core coating material is a vinyl polymer and particularly is polyvinyl acetate, the present delivery system comprises:

A. At least one first solid natural or artificial high intensity sweetener selected from the group consisting of amino acid-based sweeteners, chloro derivatives of sucrose, dihydroflavinol, hydroxyguaiacol esters, L-aminodicarboxylic acid gem-diamines, L-aminodicarboxylic acid aminoalkenoic acid ester amides, dipeptide sweeteners, glycyrrhizin, saccharin and its salts, acesulfame salts, cyclamates, steviosides, talin, dihydrochalcone compounds and mixtures thereof;

B. An emulsifier selected from the group consisting of lecithin, stearates, ester derivatives of stearates, palmitates, ester derivatives of palmitates, oleates, ester derivatives of oleates, polysorbate, sodium lauryl sulfate, glycerides, ester derivatives of glycerides, sucrose polyesters, polyglycerol esters, and animal waxes, vegetable waxes, synthetic waxes, petroleum wax and mixtures thereof;

C. A first inner coating of polyvinyl acetate present in amounts of about 20% to about 93% by weight of the total composition and having a molecular weight of about 2,000 to about 14,000 and preferably about 2,000 to about 12,000; and D. A second outer coating of a hydrophilic polymer containing a second sweetener, the outer coating prepared from a solution of the hydrophilic polymer and the second sweetener, with the second sweetener being present in the polymer solution in an amount ranging from about 10% to about 25% by weight as based on said solution, and preferably from about 3% to about 15% as based on said solution, the outer coating present in an amount of from about 5% to about 50% by weight of the inner coating.

More particularly, the delivery system of the present invention comprises the first sweetener in an amount of from about 1% to about 50% by weight of the final delivery system, the first coating in an amount of from about 20% to about 93% by weight thereof, the emulsifier in an amount of from about 0.5% to about 20% by weight thereof, the second coating in an amount of from about 15% to about 50% by weight of the first coating, and the second sweetener in an amount of about 1% to about 30% by weight as based on the solution formed with said second coating and said second sweetener. The first sweetener may preferably be present in an amount from about 10% to about 25% by weight of the core, and the second sweetener may be preferably present in an amount ranging from about 3% to about 15% by weight of the second coating.

Naturally, the specific proportions may vary from the exemplary ranges recited above within the scope of the invention.

The emulsifier may be selected from mono-, di and triglyceride esters of fatty acids, polyglycerol esters and the like. More particularly, the emulsifier may be selected from the group consisting of lecithin, stearates, ester derivatives of stearates, palmitates, ester derivatives of palmitates, oleates, ester derivatives of oleates, polysorbate, sodium lauryl sulfate, glycerides, sucrose polyesters, polyglycerol esters and mixtures thereof. Of the emulsifiers useful in the preparation of the first coating, glyceryl monostearate is the most preferred emulsifier. In a preferred embodiment, the emulsifier may be present in an amount of from about 2% to about 15% by weight.

Both the core and the second coating of the present invention may comprise a hydrocolloid. Suitable hydrocolloids may be generally selected from the group consisting of gums, pectins, alginates, mucilages, film forming carbohydrates, and mixtures thereof. Specifically, the hydrocolloid may be material selected from the group consisting of gum arabic, tragacanth, karaya, ghatti, agar, alginates, carrageenans, fucellan, psyllium, and mixtures thereof. The hydrocolloid may also be selected from polyvinyl pyrrolidone, gelatin, dextran, xanthan, curdan, cellulose, methylcellulose, ethylcellulose, hydroxyethyl cellulose, hydroxypropyl cellulose, hydroxypropyl methylcellulose, carboxymethyl cellulose, low methoxy pectin, propylene glycol alginate, polydextrose, modified starch, maltodextrin, and mixtures thereof.

The second sweetener may be selected from natural and synthetic intense sweeteners, and in a preferred embodiment may comprise one of the same group of sweeteners useful as the first sweetener herein. It is one of the advantages of the present invention that the second coating can provide improved protection for the active and at the same time greatly enhance up front sweetness release owing in part to the presence of the second sweetener, and yet is applied and is present in an amount that is substantially reduced from the fat/wax coating that is presently in successful use as the outer coating for the polyvinylacetate-encapsulated core material.

The delivery system is prepared by preparing the core coating material as a liquid and homogeneously mixing the sweetener therewith. In the instance where the core coating is prepared from polyvinyl acetate, preparation proceeds by melting the desired ratios of polyvinyl acetate and emulsifier and mixing them at a temperature of about 85° C. for a short period of time, e.g., 5 minutes or more. Once these materials are sufficiently melted and a homogenous mixture is obtained, the proper amount of solid sweetener is added and blended into the molten mass thoroughly for an additional short period of mixing. The resultant mixture is a semi-solid mass which is then cooled to obtain a solid, e.g., at 20° C., and ground to a U.S. standard mesh size of about 30 to about 200 (600–75 microns).

The preparation of the present composite continues with the preparation of a solution of the second coating by the formation of an aqueous solution mixture of the second sweetener and the hydrophilic coating material. Accordingly, an aqueous solution of the hydrophilic coating material is prepared, for example, by placing the hydrophilic coating material in solution in deionized water. The sweetener is then added to the resulting solution to form the aqueous solution mixture. Throughout the preparation of the second outer coating, the temperature may be maintained at about 50° to about 60° C.

Thereafter the particles comprising the core of the present delivery system are coated with the second outer coating. The application of the second outer coating to the core particle may be accomplished by the same techniques disclosed in U.S. Pat. No. 4,384,004 to Cea et al. for materials of this type, and accordingly a variety of coating techniques including fluidized bed coating procedures are useful. The preferred coating procedure is the fluidized bed procedure wherein particles of the core material are suspended in an apparatus that creates a strong upward air current or stream in which the particles move. The stream passes through a zone of finely atomized coating material which causes the passing particles to be coated, after which the coated particles move from the upward stream and travel downward in a fluidized condition countercurrent to a flow of heated fluidized gas whereupon they are dried. The particles may reenter the upward stream for a further coating or may be withdrawn from the coating apparatus. The foregoing method and apparatus are known as the Wurster Process and are set forth in detail in the following U.S. Patents, the disclosures of which are incorporated herein by reference: U.S. Pat. No. 3,089,824; U.S. Pat. No. 3,117,027; U.S. Pat. No. 3,196,827; U.S. Pat. No. 3,241,520; and U.S. Pat No. 3,253,944.

The application of the second coating may be conducted at temperature levels that are reduced from those of most encapsulation processes and are accordingly less likely to damage the treated particles. In particular, the second coating process may operate at inlet temperatures on the order of 100° to 125° F., so that relatively mild heating of the particles takes place during the coating process. Naturally, the temperature may vary and the selection of an optimum temperature resides within the skill of the art.

As described above, the second outer coating is prepared for use by the formation of a liquid capable of being uniformly atomized. Thus, the water soluble hydrocolloid materials may be prepared as aqueous solutions. If desired, other ingredients such as plasticizers may be added to improve the properties of the final coating. Suitable plasticizers include the glyceryl ester of sebacic acid, diethyl phthalate, glyceryl triacetate, tributyl citrate, acetylated monoglyceride, citric acid ester of monodiglyceride, adipate ester, and others. The plasticizers may be added in known effective amounts within the scope of the invention.

The instant delivery system can be incorporated in a number of ingestible products such as confections and the like, as well as chewing gum compositions, pharmaceutical preparations and denture products.

The resultant product of this invention is in powder or granulated form. The particle size is not critical to the delivery system and can be adjusted to accommodate a particular desired release rate and mouthfeel, depending on the vehicle, e.g., chewing gum, confection or pharmaceutical in which it is incorporated. The product can be used as is for various applications, e.g., as a topping on baked goods or as an additive in a denture adhesive. The coating matrix is useful for a variety of core materials in addition to sweeteners, such as spray dried flavors, drugs and other particulate materials which require a coating for protection, controlled release or for taste-masking.

The core material can be selected from a wide variety of materials such as sweeteners, medicaments, drugs, flavoring agents and the like. These materials can be used either singly or in combination in either a single or multiple delivery system. That is, one or more of these materials may be present within one coating matrix or separately coated by the matrix and employed alone or in combination in a final product.

Either sweetener component may be selected from solid natural or synthetic sweeteners capable of imparting high intensity sweetness. These sweeteners are selected from the group consisting of amino acid-based sweeteners, chloro derivatives of sucrose, dihydroflavinol, hydroxyguaiacol esters, L-amino dicarboxylic acid gem-diamines, L-aminodicarboxylic acid aminoalkenoic acid ester amides, dipeptide sweeteners, glycyrrhizin, saccharin and its salts, acesulfame salts, cyclamates, steviosides, talin, dihydrochalcone compounds and mixtures thereof.

The sweeteners which are part of the delivery system may be used in amounts necessary to impart sweetness and preferably in amounts of about 1% to about 30% by weight of the delivery system. Aspartame, saccharin, acesulfame and its salts are the preferred sweeteners and may be used in amounts of about 1% to about 50% and about 1% to 50%, respectively, by weight of the delivery system. The preferred amounts of these sweeteners are about 2 to about 25%, most preferably about 5 to about 15%. Auxiliary sweeteners may be used in the final product, i.e., chewing gum composition, in conventional amounts standard in the industry.

A particularly effective combination of sweeteners is aspartame, sodium saccharin and acesulfame K (potassium acesulfame). Saccharin and its salts and acesulfame salts may be employed in amounts of about 5 to about 50% by weight of the delivery system. Aspartame is used in amounts up to about 15% by weight when used in this combination. One or more of the sweeteners may be in the encapsulated form prior to incorporation in the delivery system, thus delaying the release of the sweetener and lengthening the perceptible sweetness and/or staggering their release. Thus, the sweeteners may be incorporated such that they release sequentially.

It has also been discovered that the incorporation of the combination of two or more sweeteners used alone or as part of the delivery system improves the sweetness intensity as a result of synergism. Exemplary examples of synergistic combinations are: saccharin/aspartame; saccharin/potassium acesulfame; saccharin/aspartame/potassium acesulfame. These sweeteners can also be added to the final food, confectionery, drug or personal product independently of the delivery system. Thus, a good product may have sweetness imparted thereto attributable to the delivery system sweetness as well as those auxiliary sweeteners independent of the delivery system. These combinations of sweeteners have also been discovered to impart a long-lasting flavor effect to the food product such as chewing gum.

Useful flavoring agents may be chosen from synthetic flavoring liquids and/or liquids derived from plants, leaves, flowers, fruits, etc., and combinations thereof. Representative flavoring liquids include: spearmint oil, cinnamon oil, oil of wintergreen (methylsalicylate) and peppermint oils. Also useful are artificial, natural or synthetic fruit flavors such as citrus oil including lemon, orange, grape, lime and grapefruit and fruit essences including apple, strawberry, cherry, pineapple and so forth.

The amount of flavoring agent employed is normally a matter of preference subject to such factors as flavor type, base type and strength desired. In general, amounts of about 0.05% to about 3.0% by weight of the final chewing gum composition are usable with amounts of about 0.3% to about 2.5% being preferred and about 0.7% to about 2.0% being most preferred.

With regard to chewing gum formulations in which the novel delivery system is employed, the amount of gum base employed will vary greatly depending on various factors such as the type of base used, consistency desired and other components used to make the final product. In general, amounts of about 5% to about 85% by weight of the final chewing gum composition are acceptable for use in chewing gum composition with preferred amounts of about 15% to about 70% by weight. The gum base may be any water-insoluble gum base well known in the art. Illustrative examples of suitable polymers in gum bases include both natural and synthetic elastomers and rubbers. For example, those polymers which are suitable in gum bases include, without limitation, substances of vegetable origin such as chicle, jelutong, gutta percha and crown gum. Synthetic elastomers such as butadiene-styrene copolymers, isobutylene-isoprene copolymers, polyethylene, polyisobutylene and polyvinylacetate and mixtures thereof are particularly useful.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene or beta-pinene; terpene resins including polyterpene and mixtures thereof. The solvent may be employed in an amount ranging from about 10% to about 75% and preferably about 45% to about 70% by weight to the gum base.

A variety of traditional ingredients such as plasticizers or softeners such as lanolin, stearic acid, sodium stearate, potassium stearate, glyceryl triacetate, glycerine and the like, for example, natural waxes, petroleum waxes, such as polyurethane waxes, paraffin waxes and microcrystalline waxes may also be incorporated into the gum base to obtain a variety of desirable textures and consistency properties. These individual additional materials are generally employed in amounts of up to about 30% by weight and preferably in amounts of from about 3% to about 20% by weight of the final gum base composition.

The chewing gum composition may additionally include the conventional additives of flavoring agents, coloring agents such as titanium dioxide; emulsifiers such as lecithin and glyceryl monostearate; and additional fillers such as aluminum hydroxide, alumina, aluminum silicates, calcium carbonate, and talc and combinations thereof. These fillers may also be used in the gum base in various amounts. Preferably, the amount of fillers when used will vary from about 4% to about 30% by eight of the final chewing gum.

In the instance where auxiliary sweeteners are utilized in addition to those in the delivery system, the present invention contemplates the inclusion of those sweeteners well known in the art, including both natural and artificial sweeteners. Thus, additional sweeteners may be chosen from the following non-limiting list: sugars such as sucrose, glucose (corn syrup), dextrose, invert sugar, fructose, and mixtures thereof, saccharine and its various salts such as the sodium or calcium salt; cyclamic acid and its various salts such as the sodium salt; the dipeptide sweeteners such as aspartame; dihydrochalcone compounds, glycyrrhizin; Stevia Rebaudiana (Stevioside); chloro derivatives of sucrose; dihydroflavinol; hydroxyguaiacol esters; L-amino dicarboxylic acid gem-diamines; L-aminodicarboxylic acid aminoalkenoic acid ester amides; and sugar alcohols such as sorbitol, sorbitol syrup, mannitol, xylitol, and the like. Also contemplated as an additional sweetener is the nonfermentable sugar substitute (hydrogenated starch hydrolysate) which is described in U.S. Reissue Pat. No. 26,959. Also contemplated is the synthetic sweetener 3,6-dihydro-6-methyl-l-1,2,3-oxathiazin-4-one-2,2dioxide, particularly the potassium (Acesulfame-K), sodium and calcium salts thereof as described in German Patent No. 2,001,017.7.

Suitable flavorings including both natural and artificial flavors, and mints such as peppermint, menthol, artificial vanilla, cinnamon, various fruit flavors, both individual and mixed, and the like are contemplated. The flavorings are generally utilized in amounts that will vary depending upon the individual flavor and may, for example, range in amounts of about 0.5% to about 3% by weight of the final chewing gum composition weight. The flavorings may be present in the delivery system, in the chewing gum composition itself, or both.

The colorants useful in the present invention include the pigments such as titanium dioxide, that may be incorporated in amounts of up to about 1% by weight, and preferably up to about 6% by weight. Also, the colorants may include other dyes suitable for food, drug and cosmetic applications, and known as FD&C dyes and the like. The materials acceptable for the foregoing spectrum of use are preferably water-soluble. Illustrative examples include indigoid dye, known as FD&C Blue No. 2, which is the disodium salt of 5,5'-indigotindisulfonic acid. Similarly, the dye known as FD&C Green No. 1 comprises a triphenylmethane dye and is the monosodium salts of 4-[4-N-ethyl-p-sulfobenzylamino)diphenylmethylene]-[1-(N-ethyl-N-p-sulfoniumbenzyl)-2-5-cyclohexadieneimine]. A full recitation of all FD&C and D&C and their corresponding chemical structures may be found in the *Kirk-Othmer Encyclopedia of Chemical Technology*, in Volume 5, pages 857-884, which text is accordingly incorporated herein by reference.

The chewing gums of the invention may be in any form known in the art, such as stick gum, slab gum, chunk gum, shredded gum, hard-coated gum, tableted gum, as well as center-filled gum.

The process of preparing the inventive chewing gum compositions is as follows. The gum base is melted (about 85° to about 90° C.), cooled to 78° C. and placed in a pre-warmed (60° C.) standard mixing kettle equipped with sigma blades. The emulsifier is then added and mixed in. Next, a portion of the sorbitol and the glycerin is added and mixed in for an additional 3 to 6 minutes. The mixing kettle is cooled and mannitol, and the remainder of the sorbitol and glycerin are then added and mixing is continued. At the time, the unflavored chewing gum temperature is about 39°-50° C. Flavor oil is then added and incorporated into the base and the mixing is continued. Finally, the delivery system containing the sweetener material is added and mixed for an additional 1 to 10 minutes. The delivery system is added as the last ingredient. The final gum temperature is about 39°-50° C. The chewing gum composition is then discharged from the kettle, rolled, scored and formed into chewing gum pieces.

Accordingly, a further embodiment of the present invention relates to a method of preparing a chewing gum composition having improved sustained sweetener release properties which comprises:
(1) Preparing a sweetener delivery system wherein the sweetener is protected by an encapsulation prepared by the process comprising:
  (a) entrapping a first sweetener in a core coating comprising the steps of uniformly mixing the core coating and the sweetener;
  (b) grinding the resultant mixture to the desired particle size;
  (c) coating the resulting particles with a second coating material containing a second sweetener uniformly dispersed as droplets therein, by a fluidized bed-type process; and
  (d) recovering the final plural coated particles; and
(2) Adding the resultant delivery system to a homogeneous mixture of a gum base and remaining chewing gum ingredients; and
(3) Forming the resultant mixture into suitable chewing gum shapes.

In the instance where the core coating is polyvinyl acetate, the first sweetener may be entrapped in the polyvinyl acetate coating by the steps of melting and blending the polyvinyl acetate with an emulsifier and dispersing the sweetener uniformly therein; and cooling the mixture at ambient temperature while continuing to mix.

The following examples serve to provide further appreciation of the invention but are not meant in any way to restrict the effective scope of the invention. All percentages throughout the specification are by weight percent of the final delivery system unless otherwise indicated.

EXAMPLE 1

In this example, a representative formulation of the sweetener delivery system of the present system was prepared in accordance with the method described hereinabove. Specifically, a quantity of 500 grams of the core was prepared in accordance with the teachings of the '742 application, and comprised a polyvinylacetate encapsulation containing 16.29% by weight of aspartame. A quantity of 750 grams of the second coating was prepared with the second sweetener by the addition of gelatin to deionized water to form a solution. The sweetener acesulfame-K was then added to the resulting solution to form the aqueous coating solution. The final coating solution contained 10% gelatin, 4.65% acesulfame-K and 85.35% deionized water. The coating was then applied to the core by a fluidized bed coating procedure and when dried, the resulting particles were determined to contain 5.72% acesulfame-K and 13.35% aspartame, both by weight of the final delivery system.

EXAMPLE 2

A further formulation of the sweetener delivery system of the present invention was prepared in the same fashion as with the formulation of Example 1. Specifically, a quantity of 600 grams of the core was prepared and comprised a polyvinylacetate encapsulation containing 16.2% acesulfame-K. A quantity of 900 grams of the second coating was prepared with the second sweetener comprising sodium saccharin and having a final solution containing 10% gelatin, 5.88% saccharin and 84.12% deionized water. The second coating was applied to the core by a fluidized bed coating procedure, and when dried, the particles were determined to contain 7.1% saccharin and 13.1% acesulfame-K, both by weight of final delivery system.

EXAMPLE 3

A further formulation of the present sweetener delivery system was prepared, which, in this instance, was based upon an alternate hydrophilic coating material for the core. Thus, 500 grams of the core was prepared by the formation of a solution of 30% gum arabic, 35% mannitol and 35% aspartame. The core was formed by first mixing the mannitol and aspartame, coating this mixture with the gum arabic solution and thereafter continuing to coat the mixture with gum arabic and conducting an agglomeration in this fashion. The core was then coated with 285.7 grams of an outer coating prepared from gum arabic and acesulfame-K. The outer coating comprised 20% acesulfame-K, 15% gum arabic and 65% deionized water.

The outer coating was applied by fluidized bed coating procedure, and when dried, the resulting particles were determined to contain 26.66% aspartame and 9.53% acesulfame-K.

EXAMPLE 4

Chewing gum compositions were prepared in accordance with the present invention for the purpose of comparing the properties of sweetener release and sweetness intensity with the sweetener release of gum compositions prepared within conventional parameters of ingredients wherein the sweeteners were included in the form.

Accordingly, two compositions having the sweetener delivery system of the present invention were prepared and are designated formulation Examples A and C. The cores of Examples 1 and 3 were prepared in accordance with the teachings of the '743 application. Two compositions were prepared as controls with the same sweeteners included in free form. The proportion of ingredients of Examples A–D are listed in Table 1, below.

TABLE 1

| INGREDIENT | AMOUNT (WEIGHT PERCENT) | | | |
|---|---|---|---|---|
| Examples | A | B | C | D |
| Gum Base | 26.00 | 26.00 | 26.00 | 26.00 |
| Carbohydrates | | | | |
| Mannitol/Sorbitol | 62.20 | 62.68 | 60.91 | 62.42 |
| Softeners | 9.35 | 9.35 | 9.35 | 9.35 |
| Flavor | 1.70 | 1.70 | 1.70 | 1.70 |
| Color | — | — | 0.17 | 0.17 |
| Free Aspartame | — | 0.20 | — | 0.25 |
| Free Acesulfame-K | — | 0.07 | — | 0.11 |
| Encapsulations | | | | |
| Example 3 | 0.75 | — | — | — |
| Example 1 | — | — | 1.87 | — |

EXAMPLE 5

Comparative blind chew panel testing was conducted with formulation Examples A and B of the chewing gum compositions prepared in Example 4, above.

The test samples of gum were given to a chew panel whose members all chew on a regular basis, for the purpose of screening the samples. During the experiment, each panelist was asked to evaluate the prototypes by the attributes listed below and to render an opinion based on the following numerical scale:

| 0 | 10 | 20 | 30 | 40 | 50 | 60 | 70 | 80 | 90 | 100 |
|---|---|---|---|---|---|---|---|---|---|---|
| VERY POOR | | | | | | | | | | EXCELLENT |
| LOW (INTENSITY) | | | | | | | | | | HIGH (INTENSITY) |

The panelists were asked to rate the samples at intervals of 30 seconds, 2, 6, 10 and 15 minutes. The attribute rated was sweetness intensity.

The results of the ratings assigned by each of the panelists to each of inventive Example A and control Example B were averaged together and then compared as to sweetness intensities and delivery. The data are expressed in graphical form in the FIG. 1.

Figure 1:
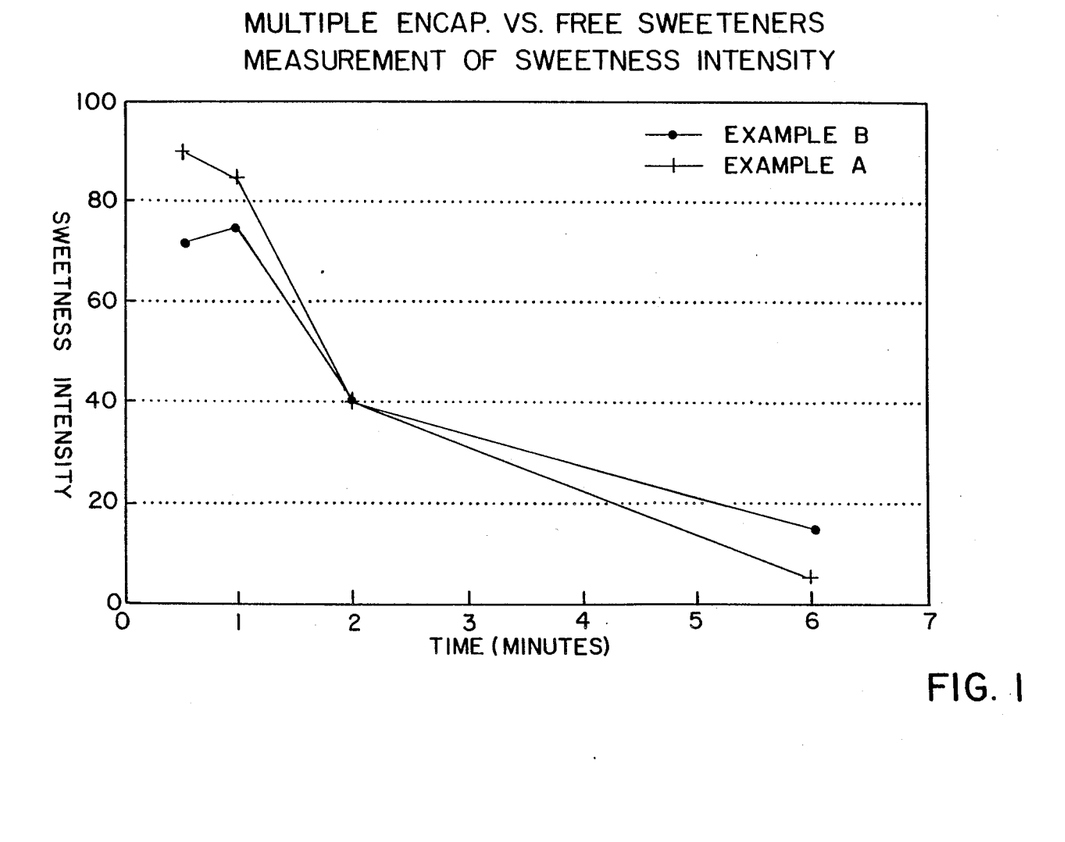
FIG. 1 is a graph of the results of comparative chew panel testing measuring the sweetness intensity of gum containing the inventive sweetener delivery system and a gum prepared with the sweeteners in free form.

As can be seen from FIG. 1, the formulation of the invention offered a greater initial sweetness intensity. This is believed to be due to the gum arabic outer matrix which may increase the solubility of aspartame in the core. The results of this test illustrate the improved up front sweetness delivery of the inventive sweetener delivery system.

EXAMPLE 6

A comparative chew panel was conducted with gum Examples C and D, to determine the release of acesulfame-K, which in Example C, is disposed in the outer coating. The purpose of this experiment was to establish that the present delivery system achieved the sequential delivery of sweeteners. The protocol of the panel was the same as with Example 5, above, except as to the attribute being measured, and the results are set forth graphically in FIG. 2.

Figure 2:
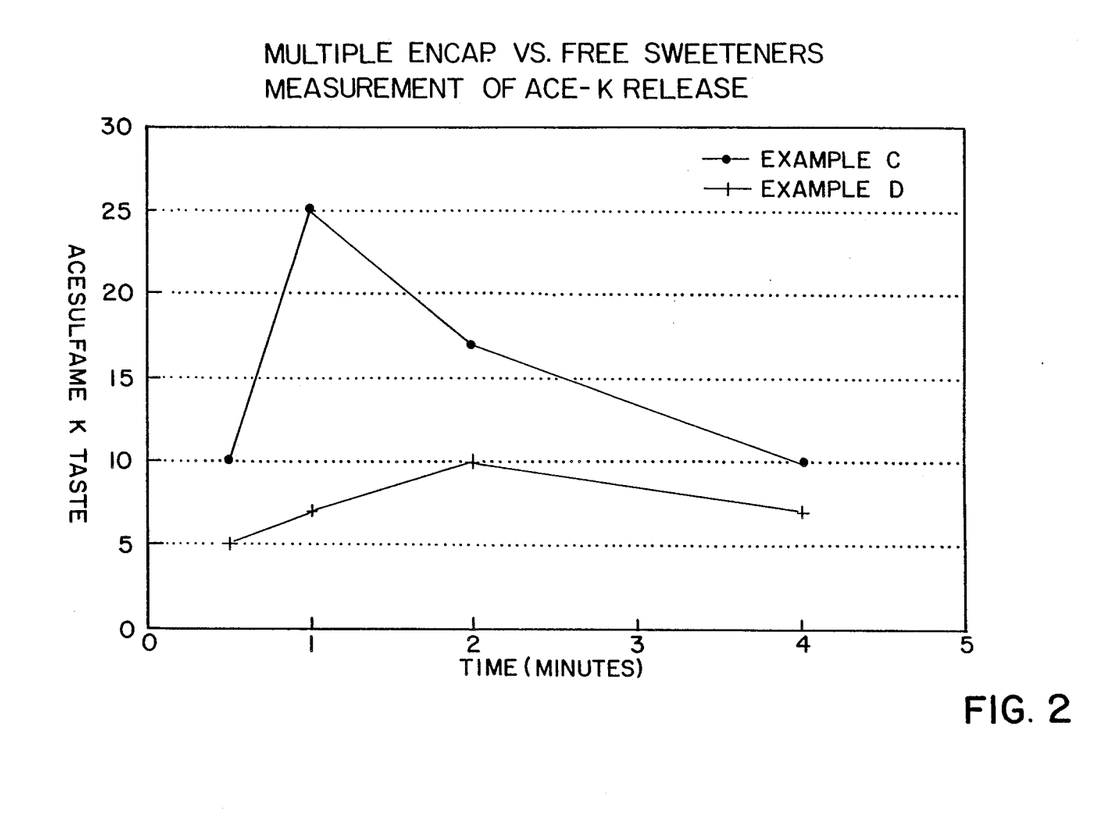
FIG. 2 is a graph of the results of comparative chew panel testing measuring the acesulfame K taste and release of gum containing the inventive sweetener delivery system and a gum prepared with the sweeteners in free form.

Referring to FIG. 2, the exact attribute being measured was the harshness or off note of the sweetener. In the instance of Example C, the individual release of acesulfame-K resulted in the perception of greater harshness or taste characteristic of acesulfame-K alone, whereas the direct synergy of acesulfame-K and aspartame which occurs with comparative formulation D yields a less harsh taste that is reflected in lower values in the Figure. The synergy between acesulfame-K and aspartame is well-known as set forth in U.S. Pat. No. 4,158,068 to Von Rymon Lipinski et al., the disclosure of which is incorporated herein by reference. It is to be emphasized that this test was conducted solely for the purpose of proving demonstratively that the present delivery system effectively achieves the sequential delivery of a different sweetener. Naturally, preparations useful for consumption would be formulated with sweeteners that are complementary with each other so that any shifts in sweetener perception would be pleasant.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A sweetener delivery system capable of providing greater up front sweetness while modulating sweetener release and providing greater protection for the sweetener, said sweetener delivery system comprising:
    A. at least one first solid natural or artificial high intensity sweetener selected from the group consisting of amino acid-based sweeteners, chloro derivatives of sucrose, dihydroflavinol, hydroxyguaiacol esters, L-aminodicarboxylic acid gem-diamines, L-aminodicarboxylic acid aminoalkenoic acid ester amides, dipeptide sweeteners, glycyrrhizin, saccharin and its salts, acesulfame salts, cyclamates, steviosides, talin, dihydrochalcone compounds and mixtures thereof;
    B. a first inner coating selected from hydrophobic and hydrophilic coating materials, said inner coating and said first sweetener mixed and prepared to form a core with said first sweetener present in an amount of from about 1% to about 50% by weight of said core; and
    C. a second outer coating of a hydrophilic polymer containing a second sweetener, said second outer coating prepared from a solution of the hydrophilic polymer and said second sweetener, with said second sweetener being present in the polymer solution in an amount ranging from about 10% to about 25% by weight of said solution, the outer coating present in an amount of from about 5% to about 50% by weight of said inner coating.

2. A sweetener delivery system capable of providing greater up front sweetness while modulating sweetener release and providing greater protection for the sweetener, said sweetener delivery system comprising:
   A. at least one first solid natural or artificial high intensity sweetener selected from the group consisting of amino acid-based sweeteners, chloro derivatives of sucrose, dihydroflavinol, hydroxyguaiacol esters, L-aminodicarboxylic acid gem-diamines, L-aminocarboxylic acid aminoalkenoic acid ester amides, dipeptide sweeteners, glycyrrhizin, saccharin and its salts, acesulfame salts, cyclamates, steviosides, talin, dihydrochalcone compounds and mixtures thereof;
   B. an emulsifier selected from the group consisting of lecithin, stearates, ester derivatives of stearates, palmitates, ester derivatives of palmitates, oleates, ester derivatives of oleates, glycerides, ester derivatives of glycerides, sucrose polyesters, polyglycerolesters, and animal waxes, vegetable waxes, synthetic waxes, petroleum wax and mixtures thereof;
   C. a first inner coating of polyvinyl acetate present in amounts of about 20% to about 93% by weight of the total composition and having a molecular weight of about 2,000 to about 14,000; and
   D. a second outer coating of a hydrophilic polymer containing a second sweetener, the outer coating prepared from a solution of the hydrophilic polymer and the second sweetener, with the second sweetener being present in the polymer solution in an amount ranging from about 20% to about 25% by weight of said solution, the outer coating present in an amount of from about 5% to about 50% by weight of the inner coating.

3. The sweetener delivery system of claims 1 or 2 wherein said second sweetener is present in an amount ranging from about 3% by weight to about 15% by weight of the second coating.

4. The sweetener delivery system of claim 2 wherein said first sweetener is present in an amount of from about 1% to about 50% by weight of the delivery system.

5. The sweetener delivery system of claims 1 or 2 wherein said first sweetener comprises aspartame in the amount of from about 1% to about 50% by weight of the delivery system.

6. The sweetener delivery system of claims 1 or 2 wherein said first sweetener comprises saccharin and its salts in the amount of from about 1% to about 50% by weight of the delivery system.

7. The sweetener delivery system of claims 1 or 2 wherein said first sweetener comprises a combination of up to about 25% of aspartame and about 1.0% to about 50% of saccharin and its salts by weight of the delivery system.

8. The sweetener delivery system of claim 7 wherein the first sweetener additionally contains about 1% to about 50% of potassium acesulfame by weight of the delivery system.

9. The sweetener delivery system of claim 2 wherein said emulsifier is present in an amount of from about 0.5% to about 20% by weight of the delivery system.

10. The sweetener delivery system of claims 1 or 2 wherein said second outer coating comprises a hydrocolloid.

11. The sweetener delivery system of claim 10 wherein said second outer coating is selected from the group consisting of gums, pectins, alginates, mucilages, film forming carbohydrates, and mixtures thereof.

12. The sweetener delivery system of claim 11 wherein said second outer coating is selected from the group consisting of gum arabic, tragacanth, karaya, ghatti, agar, alginates, carrageenans, fuceilan, psyllium, and mixtures thereof.

13. The sweetener delivery system of claim 11 wherein said second outer coating is selected from the group consisting of polyvinyl pyrrolidone, gelatin, dextran, xanthan, curdan, cellulose, methylcellulose, ethylcellulose, hydroxyethyl cellulose, hydroxypropyl cellulose, hydroxypropyl methylcellulose, carboxymethyl cellulose, low methoxy pectin, propylene glycol alginate, and mixtures thereof.

14. The sweetener delivery system of claims 1 or 2 wherein said second outer coating is present in an amount of from about 15% to about 50% by weight of said first coating.

15. The sweetener delivery system of claim 2 wherein said polyvinyl acetate has a molecular weight ranging from about 2,000 to about 12,000.

16. The sweetener delivery system of claim 9 wherein the emulsifier is selected from the group consisting of glyceryl monostearate, glyceryl distearate, glyceryl tristearate, the fatty acid esters thereof, and mixtures thereof, and is present in amounts of about 2% to about 15% by weight of the delivery system.

17. The sweetener delivery system of claim 2 wherein the polyvinyl acetate is blended with a material selected from the group consisting of resins, rosins, terpenes, elastomers, waxes and mixtures thereof.

18. The sweetener delivery system of claims 1 or 2 wherein both the first and second sweeteners are natural or artificial high intensity sweeteners and are each selected from the group consisting of amino acid-based sweeteners, dipeptide sweeteners, glycyrrhizin, saccharin and its salts, acesulfame salts, cyclamates, steviosides, talin, sucralose, dihydrochalcone compounds and mixtures thereof.

19. The sweetener delivery system of claim 18 wherein the sweetener is selected from the group consisting of sodium saccharin, aspartame, talin, and acesulfame-K.

20. The sweetener delivery system of claims 1 or 2 in solid particulate form.

21. A chewing gum composition capable of releasing increased amounts of sweetness evenly over a longer release time comprising a gum base and a sweetener delivery system capable of modulating sweetener release and providing greater protection for the sweetener, said sweetener delivery system comprising:
   A. at least one solid natural or artificial high intensity sweetener selected from the group consisting of amino acid-based sweeteners, chloro derivatives of sucrose, dihydroflavinol, hydroxyguaiacol esters, L-aminodicarboxylic acid gem-diamines, L-aminodicarboxylic acid aminoalkenoic acid ester amides, dipeptide sweeteners, glycyrrhizin, saccharin and its salts, acesulfame salts, cyclamates, steviosides, talin, dihydrochalcone compounds and mixtures thereof;
   B. a first inner core prepared from a coating selected from the group consisting of hydrophobic and hydrophilic coating materials, the sweetener and the core prepared with the sweetener present in an amount of from about 1% to about 50% by weight of said core; and C. a second outer coating of a hydrophilic polymer containing a second sweetener, the coating prepared from a solution of the hydrophilic polymer and the second sweetener, with the second sweetener being present in the polymer solution in an amount ranging from about 10% to about 25% by weight of said solution, the outer coating present in an amount of from about 5% to about 50% by weight of the first coating.

22. A chewing gum composition capable of releasing increased amounts of sweetness evenly over a longer release time comprising a gum base and a sweetener delivery system capable of modulating sweetener release and providing greater protection for the sweetener, said sweetener delivery system comprising:

A. at least one first solid natural or artificial high intensity sweetener selected from the group consisting of amino acid-based sweeteners, chloro derivatives of sucrose, dihydroflavinol, hydroxyguaiacol esters, L-aminodicarboxylic acid gem-diamines, L-aminodicarboxylic acid aminoalkenoic acid ester amides, dipeptide sweeteners, glycyrrhizin, saccharin and its salts, acesulfame salts, cyclamates, steviosides, talin, dihydrochalcone compounds and mixtures thereof;

B. an emulsifier selected from the group consisting of lecithin, stearates, ester derivatives of stearates, palmitates, ester derivatives of palmitates, oleates, ester derivatives of oleates, glycerides, ester derivatives of glycerides, sucrose polyesters, polyglycerolesters, and animal waxes, vegetable waxes, synthetic waxes, petroleum wax and mixtures thereof;

C. a first inner coating of polyvinyl acetate present in amounts of about 20% to about 93% by weight of the total composition and having a molecular weight of about 2,000 to about 14,000; and D. a second outer coating of a hydrophilic polymer containing a second sweetener, the outer coating prepared from a solution of the hydrophilic polymer and the second sweetener, with the second sweetener being present in the polymer solution in an amount ranging from about 20% to about 25% by weight of said solution, the outer coating present in an amount of from about 5% to about 50% by weight of the first coating.

23. The chewing gum composition of claims 21 or 22 wherein the gum base comprises an elastomer selected from the group consisting of natural rubber, synthetic rubber and mixtures thereof.

24. The chewing gum composition of claim 23 wherein the gu base elastomer is selected from the group consisting of chicle, jelutong, balata, gutta-percha, lechi-capsi, sorva, butadiene-styrene copolymers, polyisobutylene, isobutylene-isoprene copolymers, polyethylene, polyvinylacetate, and mixtures thereof.

25. The chewing gum composition of claim 24 wherein the gum base is present in amounts of about 5% to about 85% by weight of the final chewing gum composition.

26. The chewing gum composition of claims 21 or 22 further including fillers, coloring agents, flavoring agents, softeners, plasticizers, elastomers, elastomer solvents, sweetening agents and mixtures thereof.

27. A method for preparing a sweetener delivery system capable of providing greater up front sweetness while modulating sweetener release and providing greater protection for the sweetener, comprising:

(a) entrapping a sweetener in a polyvinyl acetate coating comprising the steps of melting and blending the polyvinyl acetate with an emulsifier and dispersing the sweetener uniformly therein; cooling the mixture at ambient temperature while continuing to mix;

(b) grinding the resultant mixture to the desired particle size;

(c) coating the resulting particles with a second coating material by a fluidized bed-type process; and (d) recovering the final plural coated particles.

28. A method of preparing a chewing gum composition having improved sustained sweetener release properties which comprises:

(1) preparing a sweetener delivery system by the method of claim 27;

(2) adding the sweetener delivery system prepared in Step 1 to a homogeneous mixture of a gum base and remaining chewing gum ingredients; and (3) forming the resultant mixture into suitable chewing gum shapes.

29. A hard confection including the sweetener delivery system of claims 1 or 2.

30. An oral hygiene preparation including the sweetener delivery system of claims 1 or 2.

31. An oral pharmaceutical preparation including the sweetener delivery system of claims 1 or 2.

32. A bakery product including the sweetener delivery system of claims 1 or 2.

* * * * *

UNITED STATES PATENT AND TRADEMARK OFFICE
CERTIFICATE OF CORRECTION

PATENT NO. : 4,981,698
DATED : January 1, 1991
INVENTOR(S) : Subraman Rao Cherukuri, et al It is certified that error appears in the above-indentified patent and that said Letters Patent is hereby corrected as shown below:

On the title page, item [76], change "Tommy K. Chau" should read

--Tommy L. Chau--

Signed and Sealed this

Eighth Day of February, 1994

Attest:

BRUCE LEHMAN

*Attesting Officer*   Commissioner of Patents and Trademarks